United States Patent [19]

Branemark et al.

[11] 4,261,350

[45] * Apr. 14, 1981

[54] SUPPORT MEMBER FOR PROSTHESIS

[76] Inventors: Per I. Branemark, Ädergatan 3, S-431 39 Mölndal; Bo Thuresson af Ekenstam, Vadmansgatan 16, 3tr S-412 53 Goteborg, both of Sweden

[*] Notice: The portion of the term of this patent subsequent to Jan. 3, 1995, has been disclaimed.

[21] Appl. No.: 940,086

[22] Filed: Sep. 6, 1978

[30] Foreign Application Priority Data

Sep. 27, 1977 [SE] Sweden .............................. 7710777

[51] Int. Cl.³ .............................................. A61F 5/04
[52] U.S. Cl. ............................. 128/92 BC; 128/92 B; 128/92 CA; 128/92 D
[58] Field of Search .......... 128/92 G, 92 BA, 92 BB, 128/92 BC, 92 B, 92 R, 92 CA, 92 D; 3/1.9–1.913

[56] References Cited

U.S. PATENT DOCUMENTS

| 3,255,747 | 6/1966 | Cochran et al. | 128/92 R |
| 3,979,779 | 9/1976 | Zeibig et al. | 3/1.913 |
| 4,065,817 | 1/1978 | Branemark et al. | 3/1.91 |

FOREIGN PATENT DOCUMENTS

| 1525667 | 9/1978 | United Kingdom | 3/1.9 |
| 581937 | 11/1977 | U.S.S.R. | 128/92 B |

Primary Examiner—Robert W. Michell
Assistant Examiner—C. Shedd

[57] ABSTRACT

A support member for a prosthesis comprises a tubular member adapted to be secured to a prepared bone by a cement or by screw fastener. The face of the prosthesis in contact with the bone is provided with channels, typically of trapezoidal section to ensure a good supply of blood to the bone tissue and to facilitate blood vessel and bone tissue growth. A device to expand such a support member is disclosed.

14 Claims, 7 Drawing Figures

SUPPORT MEMBER FOR PROSTHESIS

BACKGROUND OF THE INVENTION

The present invention relates to a support member for a prosthesis, particularly for a prosthesis to provide an artificial joint, the support member consisting of a tubular member for securing the prosthesis to bone tissue.

It is known permanently to reconstruct the extremities and other joints of a body such as a human body which are malformed either from birth, or due to disease or accident, in various ways.

One known technique involves the substitution of the components of a joint made from a biologically acceptable material such as metal or plastics material the material being inserted in a bore formed in the ends of the bone and being held in place by a cementing process. The conventional form of cement utilized is plastics material cement, based on polymers, which are capable of forming organic chemical monomers. These cements are prepolymerised in order to ensure sufficient plasticity to apply them. However, if the cements are to be finally cured, they need to be raised to a high reaction temperature and this, together with the side effects produced by the monomers, has a disadvantageous biological effect on the bone, killing the bone tissue. Thus, this technique, although it is satisfactory in the short term, is not suitable for long term use.

Prosthetic devices have already been satisfactorily manufactured from biologically compatible metal such as titanium and titanium alloys or vitallium.

Plastics materials have also been used to form the components of a prosthesis, although plastic prosthesis are normally only suitable for smaller joints, such as finger joints. The actual retention of the prosthesis device in the bone is a function of the cement itself, and it has been conventional to use methyl acrylic and polymethyl acrylic cements, or methyl metacrylicstyrene copolymers with or without the addition of barium sulphate. As mentioned, however, the bond thus obtained is not entirely satisfactory for the reasons outlined above.

Furthermore, a prosthesis has been proposed, intended for producing an artificial joint, having a member which can be inserted into a recess in the bone, this prosthesis comprising a tubular support member having a plurality of lateral openings disposed at spaced locations around the periphery of the support member and passing through the wall thereof, and also a prosthesis body locatable at least in part in said support member and means for securing the prosthesis body in place in the support body.

With such a prosthesis, the bone to be treated is prepared in conventional manner, and the tubular support member is then inserted in the hollow interior of the bone. A suitable cement of the kind mentioned above is introduced into the tubular support member so that it passes locally through the openings and only comes into contact with the bone at the location of these openings. The cement is cured, and the prosthesis body is positioned either prior to or during this curing and is secured in place in the tubular support member.

With such an arrangement, the only portion of the bone tissue which is in any way damaged is that portion which is touched by the cement. The cement serves to hold the tubular support member in position for a short time or moderate period of time. This is sufficient to allow the bone tissue to grow inwardly and anchor the remainder of the tubular support member in place. Thus, when the bond between the cement and the bone breaks down, as it will in due course, the bone tissue will hold the support member in place.

However, it has been found that the know prostheses do not provide satisfactorily for the growth of bone tissue around the support member. It has also proved difficult to apply suitable and necessary therapeutic aids to the support member, such as anticoagulants, chemotherapeutic aids, substances to expand the blood vessels and microbicides.

OBJECTS OF THE INVENTION

The present invention seeks to provide a support member for a prosthesis in which the above described disadvantages are obviated or reduced.

One object of the present invention is to provide a support member for a prosthesis which in use results in improved care of the adjacent bone tissue, particularly the blood supply for more rapid inward growth of bone tissue in the support member.

Another object is to improve the feasibility of applying therapeutic aids in order to prevent rejection of the prosthesis, the formation of thromboses and infection.

SUMMARY OF THE INVENTION

According to this invention there is provided a support member for a prosthesis, the support member comprising a tubular member adapted to be secured to bone tissue, the support member being provided with a plurality of peripheral channels located to be open towards the bone tissue located around the periphery of the tubular member.

Preferably the channels may have a rectangular cross section, or a parallel trapezoidal cross section.

Conveniently the channels may be provided with means for receiving thereapeutically active substances.

In one embodiment of the invention the channels are arranged to receive a spongy, resorbable material.

Conveniently the channels are defined partly by the wall of the support member and partly by strips arranged to said wall.

Advantageously the support member, besides said channels, also includes sections provided with holes arranged between the channels.

Conveniently one of the intermediate sections is provided with slots.

Preferably the support member is provided with a pressure means to increase the contact pressure against the bone tissue on which the support member is applied.

Conveniently the support member is provided with a plastic lining on the side facing away from the bone tissue.

It is envisaged that, in utilising supports in accordance with the present invention, the contact surfaces of the support member applied against the bone tissue will in some part be in very tight contact with the bone tissue so that the cement used is prevented from irritating and killing more bone tissue than is necessary for the support member to be partially secured. Alternatively the support member may be constructed so that the cement is totally precluded from contact with the bone tissue by the use of a screwing principle (FIG. 5) or a pressure means. Furthermore, this offers free channels to assist in the function of supplying blood along the entire length or the most part of the length of the support member. Finally, it is envisaged that quicker growth of the bone tissue will be achieved in this way, leading to a good result from implantation of the prosthesis.

BRIEF DESCRIPTION OF THE DRAWINGS

In order that the invention may be more readily understood, and so that further features thereof may be appreciated the invention will now be described, by way of example with reference to the accompanying drawings, in which.

DESCRIPTION OF PREFERRED EMBODIMENTS

Figure 1:
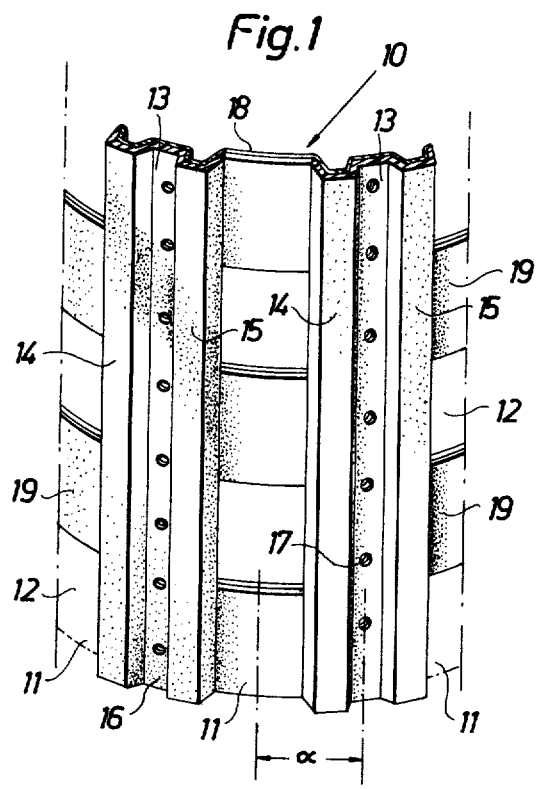
FIG. 1 is a perspective view of a part of one embodiment of the invention.

FIG. 1 shows a part of a cylindrical tubular support member 10 in accordance with the invention having a number of side wall sections 11 provided with a number of through-going holes 12. Between these sections 11 are rib sections 13 comprising two splines 14, 15 protruding from the support and defining therebetween an axially extending longitudinal recess 16. The recesses 16 are spaced around the periphery of the tubular support member 10, and form blood supply channels. Holes 17 are provided in the wall or base of each recess 16, these holes 17 being intended to receive therapeutic acids such as anticoagulants, chemotherapeutic aids and so on. The wall or base of the recess 16 and the splines 14, 15 form each section 13 in the support member in such a way that each section 13 forms a channel against the bone tissue when the member 10 is located within a hollow bone. To speed up the bonding of the support member to the securing compound or cement, the support member 10 is provided on inside with a plastics material lining 18 which reacts through suitable holes 12 with the securing compound, or cement. In the present FIG. 1 the mid-lines through the sections 11 and 13 are parallel. However, these lines may form an angle to the axis so that the support member has a helical configuration.

Supporting panels 19 in each section 11, which are the panels which define the holes 12, may be slotted along the centre line thereof, for instance, so that the support member 10 becomes resilient.

The support member may even be made conical while still retaining substantially the same design as that described above.

Figure 2:
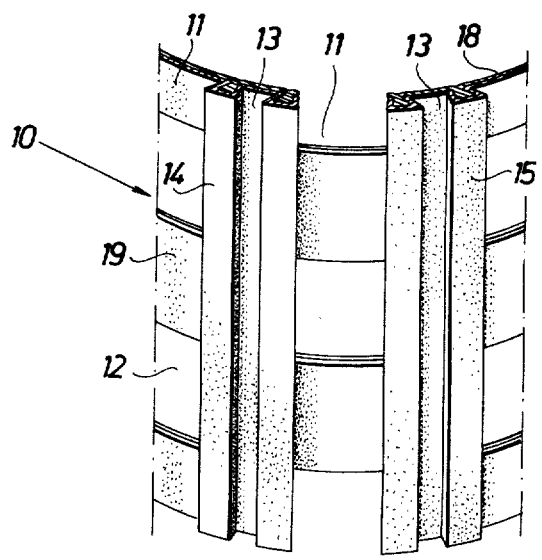
FIG. 2 is a perspective view of a part of a second embodiment of the invention.

FIG. 2 shows a similar embodiment to that shown in FIG. 1. The splines 14, 15, however, are formed so that each of the sections 13, which define the blood supply channels, has a cross section shaped liked a trapezium. The channels may then be filled with and retain a spongy material which can be resorbed by the tissue. This may also include thereapeutic aids necessary to accelerate rebuilding of the bone tissue, or aids such as anticoagulants, chemotherapeutic aids, substances to expand the blood vessels and microbicides.

The sections 11 may also be given a similar cross section in order to increase the supporting surface of the splines 14 and 15 in order further to relieve the surrounding bone tissue.

If the splines 14 and 15 are in the form of folds on the surface of the support member 10, this provides a certain flexibility for the member 10.

Figure 3:
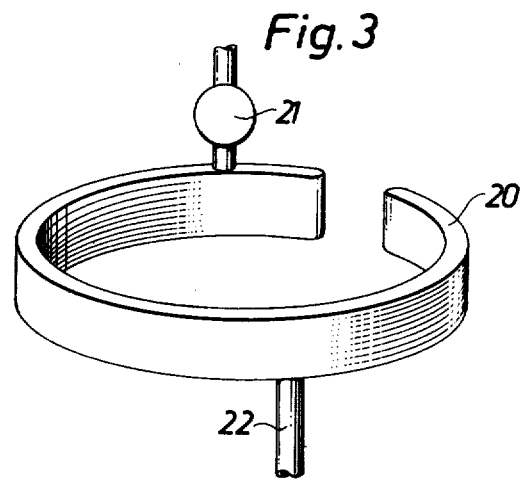
FIG. 3 is a perspective view of an additional element included in a typical support member according to the invention.

FIG. 3 shows a device intended to enable pressure to be applied on the inside of a support member 10 in order to achieve maximum contact against the bone tissue. The device comprises a hollow spring 20 which is designed, when filled with a pressure medium such as gas or liquid, to endeavour to straighten itself, thus exerting pressure on the surrounding support member 10. Pressure medium is introduced through a valve 21. If the support member 10 is long, several devices 20 may be necessary spaced along the length of the support member 20. In this case, several devices 20 are connected together by means of communicating pipes or tubes 22. The devices 20 may be arranged in advance on the support member 10 or may be inserted separately before the securing compound and prosthesis are inserted into the support member.

Figure 4:
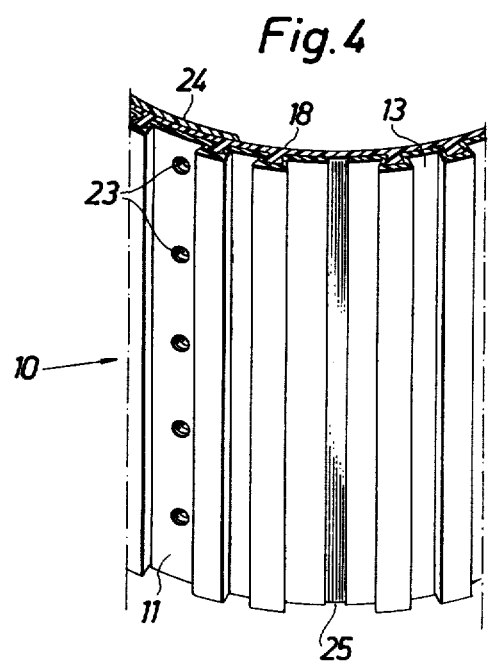
FIG. 4 is a perspective view of a part of a further embodiment of the invention.

FIG. 4 shows part of an embodiment of the invention in which sections 11 are not provided with outlets or holes 12 but with screw attachments 23 and a reinforcement 24 on the inside of the support member 10 behind the attachments 23. The screw attachments 23 are arranged to receive screws passed through the bone tissue to anchor the support member 10 to the bone tissue. The channel cross-section of the section 13 is similar to that shown in FIG. 2. One section 11 has been slotted in this embodiment and the support member expanded. The gap 25 thus produced is covered by an overlapping acylate material.

Figure 5:
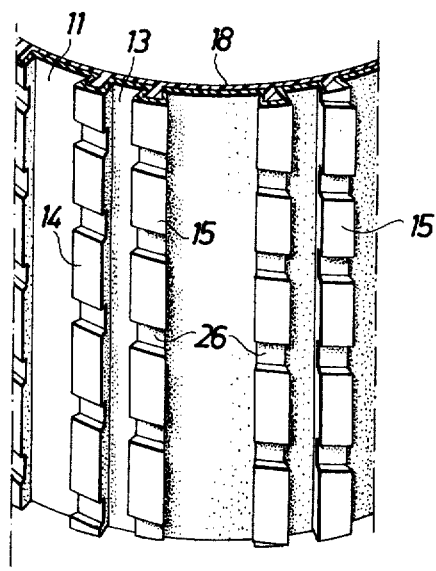
FIG. 5 is a perspective view of a part of another additional embodiment of the invention.

FIG. 5 shows an embodiment similar to that shown in FIG. 2, in which cuts 26 have been made in the strips 14 and 15 to provide a screw thread. By providing a corresponding screw thread in the bone tissue, the support member 10 can be screwed in. The thread has a depth of up to 50% of the height of the splines 14 and 15.

Figure 6:
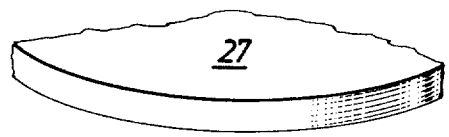
FIG. 6 is a perspective view of a part of a further embodiment of the invention.

FIG. 6 shows an embodiment of the invention for external location around bone tissue. The support member 10 has sections 11 for cementing the member to the bone tissue and sections 13 with splines 14 and 15 defining channels for spongy material with therapeutic aids for blood vessel growth. If cementing is not desired, a screw joint can be used with the aid of the threaded screws 23. In this case the support member 10 may be provided with a lid 27 intended to support the prosthesis itself.

Figure 7:
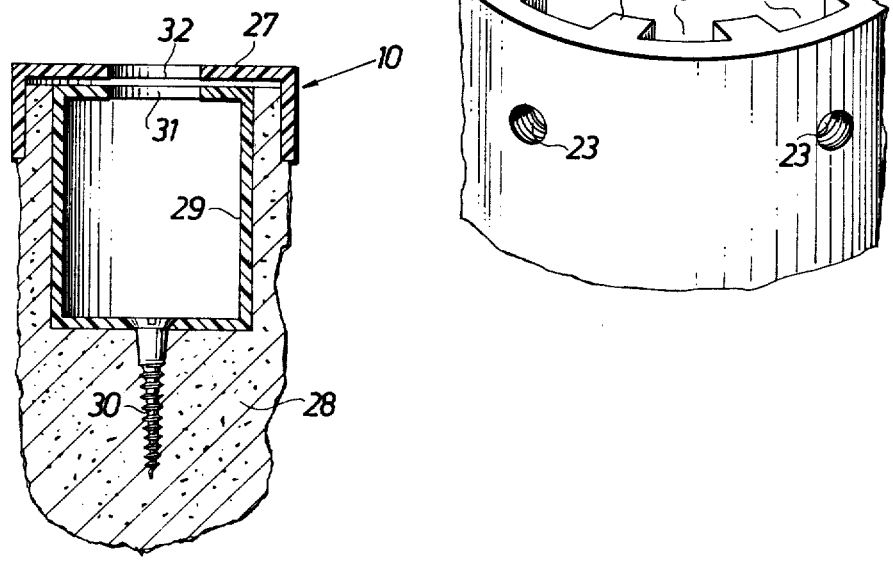
FIG. 7 is a sectional view illustrating the embodiment according to FIG. 6 used as a finger prosthesis.

FIG. 7 shows a support member 10 as shown in FIG. 6 used as a finger prosthesis. Bone tissue 28 has here been provided with a bore in which an inner sleeve 29 has been inserted and screwed into the bone tissue by means of a screw 30. The sleeve 29 is provided with an opening 31. A support member 10a is applied outside and around the sleeve 29, whereupon a hole 32 corresponding to the opening 31 is provided in the lid 27a of the member 10a. The shaft of a prosthesis is inserted through said hole 32 and opening 31 and secured to the sleeve 29 by means of fixing compound. The opening 31 and hole 32 may be threaded to ensure more reliable securing of the prosthesis.

It will be appreciated that when any of the above described prosthesis are used a plurality of recesses will be provided adjacent the bone to ensure an adequate blood supply to the bone tissue and to aid the rapid growth of bone tissue. The recesses may, if desired, contain a therapeutic aid.

Men skilled in the art will be able to make many modifications to the above described devices without departing from the spirit and scope of the present invention.

I claim:

1. A support member for a prosthesis comprising a tubular member adapted to be secured with one surface coaxial to and in contact with a bone, the tubular member being provided on said one surface with a plurality of associated pairs of ribs, each of said ribs extending radially from said one surface having substantially flat outer faces for engagement with the tissue of the bone and each of said ribs extending longitudinally from one end of said tubular member to the other end thereof, the associated ribs of each pair being spaced from each other to form an elongated channel open towards the bone tissue, each of the pairs of ribs being spaced from its next adjacent pair of ribs to form wider sections intermediate the channels, each of said intermediate sections being provided with at least one through hole therein.

2. A support member according to claim 1, wherein the channels are provided with means for receiving therapeutically active substances.

3. A support member according to claim 1, wherein the channels are provided with a spongy, resorbable material.

4. A support member according to claim 1, wherein the tubular member, at least one of the intermediate sections is provided with radially through slots for passage between the bone and the other surface of said tubular member.

5. A support member according to claim 1, wherein said tubular member is provided with a plastics material lining on the side facing away from the bone tissue.

6. A support member according to claim 1, wherein said tubular member is provided with threaded fastening means, insertable through the tubular member to secure the tubular member to a bone.

7. The support according to claim 1, including means for applying a resilient pressure on said tubular member for biasing the tubular member against said bone.

8. The support according to claim 7, wherein said resilient pressure means comprises an annular expandable member.

9. The support according to claim 1, wherein said ribs are formed by folds provided in said tubular member.

10. The support according to claim 1, wherein said ribs are formed by splines applied to the surface of said tubular tubular member.

11. The support according to claim 9 or 15, wherein the ribs are formed to provide channels having in a plane perpendicular to the longitudinal axis of the tubular member a trapezoidal cross section.

12. The support according the claim 9 or 10, wherein the ribs are formed to provide channels having substantially parallel side walls.

13. The support according to claim 9 or 10, wherein a plurality of shallow grooves are formed on the face of said ribs, said grooves being aligned in the adjacent ribs to form a helical thread on the periphery of the tubular member.

14. The support according to claim 1, including means located within said intermediate sections for securing said tubular member to the bone.

* * * * *